(12) United States Patent
Yonaha (10) Patent No.: US 11,357,672 B2
(45) Date of Patent: Jun. 14, 2022

(54) INDIVIDUALLY PACKAGED ABSORBENT ARTICLE, ABSORBENT ARTICLE, AND METHOD FOR FOLDING ABSORBENT ARTICLE

(71) Applicant: DAIO PAPER CORPORATION, Ehime (JP)

(72) Inventor: Susumu Yonaha, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 654 days.

(21) Appl. No.: 16/348,246

(22) PCT Filed: Oct. 24, 2017

(86) PCT No.: PCT/JP2017/038403
§ 371 (c)(1),
(2) Date: May 8, 2019

(87) PCT Pub. No.: WO2018/096865
PCT Pub. Date: May 31, 2018

(65) Prior Publication Data
US 2019/0254890 A1    Aug. 22, 2019

(30) Foreign Application Priority Data

Nov. 25, 2016 (JP) ............................. JP2016-229538

(51) Int. Cl.
*A61F 13/551* (2006.01)
*A61F 13/15* (2006.01)
(Continued)

(52) U.S. Cl.
CPC .......... *A61F 13/5514* (2013.01); *A61F 13/15* (2013.01); *A61F 13/15747* (2013.01);
(Continued)

(58) Field of Classification Search
CPC .... A61F 13/15; A61F 13/15747; A61F 13/47; A61F 13/472; A61F 13/476;
(Continued)

(56) References Cited

U.S. PATENT DOCUMENTS 7,695,462 B2 * 4/2010 Sato .................... A61F 13/5514
604/385.04
11,234,871 B2 * 2/2022 Kuramochi ....... A61F 13/47236
(Continued)

FOREIGN PATENT DOCUMENTS

JP        3871611         1/2007
JP      2010-082061       4/2010
(Continued)

OTHER PUBLICATIONS

International Search Report for PCT/JP2017/038403 dated Dec. 26, 2017.
(Continued)

*Primary Examiner* — Michele M Kidwell
(74) *Attorney, Agent, or Firm* — IPUSA, PLLC (57) ABSTRACT

An individually-packaged absorbent article or an absorbent article. The absorbent article (1) includes a hip-hold portion (H) that includes a side area (10) protruding from a rear side-edge of a body (8). The side area (10) includes a first protruding portion (21) that includes a portion having a largest width from a longitudinal centerline (CL) of the body (8), a first recessed portion (31) adjacent to the rear end of the first protruding portion (21), and a second recessed portion (32) adjacent to the front end of the first protruding portion (21). The absorbent article (1) is folded such that a mountain fold line (Y) is formed in the side area (10) of the hip-hold portion (H), and the mountain fold line (Y) intersects with an edge of the side area (10) of the hip-hold portion (H) at a position between a first inflection point (F1)

(Continued)

between the first recessed portion (31) and the first protruding portion (21) and a second inflection point (F2) between the first protruding portion (21) and the second recessed portion (32), and is substantially orthogonal to the longitudinal centerline (CL).

5 Claims, 8 Drawing Sheets

(51) Int. Cl.
    *A61F 13/472*     (2006.01)
    *A61F 13/47*     (2006.01)
    *A61F 13/56*     (2006.01)
    *A61F 13/476*     (2006.01)

(52) U.S. Cl.
    CPC ............ *A61F 13/47* (2013.01); *A61F 13/472* (2013.01); *A61F 13/476* (2013.01); *A61F 13/56* (2013.01); *A61F 13/15739* (2013.01); *A61F 13/5616* (2013.01); *A61F 2013/4708* (2013.01)

(58) Field of Classification Search
    CPC .. A61F 13/5514; A61F 13/56; A61F 13/5616; A61F 2013/4708
    See application file for complete search history.

(56) References Cited

U.S. PATENT DOCUMENTS

| | | | |
|---|---|---|---|
| 2004/0243087 A1* | 12/2004 | Kinoshita | A61F 13/476 604/385.04 |
| 2008/0015536 A1* | 1/2008 | Digiacomantonio | A61F 13/4704 604/385.04 |
| 2014/0288520 A1* | 9/2014 | Kuramochi | A61F 13/5616 604/385.04 |
| 2019/0290506 A1* | 9/2019 | Kuramochi | A61F 13/513 |
| 2020/0121518 A1* | 4/2020 | Kuramochi | A61F 13/472 |

FOREIGN PATENT DOCUMENTS

| | | |
|---|---|---|
| JP | 2011-172658 | 9/2011 |
| JP | 5082007 | 11/2012 |
| JP | 5947517 | 7/2016 |
| WO | 2010/038605 | 4/2010 |
| WO | 2013/024605 | 2/2013 |
| WO | 2014/157325 | 10/2014 |

OTHER PUBLICATIONS

Extended European search report for European Patent Application No. 17873189.9 dated Aug. 2, 2019.

* cited by examiner

INDIVIDUALLY PACKAGED ABSORBENT ARTICLE, ABSORBENT ARTICLE, AND METHOD FOR FOLDING ABSORBENT ARTICLE

TECHNICAL FIELD

The present invention relates to an individually-packaged absorbent article, an absorbent article, and a method for folding an absorbent article.

BACKGROUND ART

Known absorbent articles such as a pantiliner, a sanitary napkin, and an incontinence pad are made by sandwiching an absorbent between a permeable upper-side and an impermeable back-side sheet.

Also, a recent absorbent article includes a portion (hip-hold portion) for holding a hip, which is formed by increasing the length and width of rear side-portions and a rear-end portion of the absorbent article to prevent leakage of a body fluid from the absorbent article in backward and/or obliquely-backward directions.

For example, Patent Document 1 discloses a sanitary napkin including a rear flap that includes a front widening portion whose half width in the lateral direction gradually increases from a starting point at which the half width is minimum to a backward position, a middle portion having an edge parallel to a longitudinal centerline, and a rear converging portion whose half width gradually decreases toward the rear end.

Patent Document 2 discloses an absorbent article including a rear flap that includes an impermeable sheet and a nonwoven fabric stacked on a skin-contacting side of the impermeable sheet.

The rigidity of the rear flap of Patent Document 2 is increased by forming, through hot embossing, an indented pattern on the multilayer structure of the impermeable sheet and the nonwoven fabric.

Also, Patent Document 3 discloses an absorbent article that has a long length and includes a pair of three-dimensional gathers formed on sides of the absorbent article along the longitudinal direction and a pair of rear flaps extending outward in a width direction from side edges of a rear area of the absorbent article.

Here, when an absorbent article including a hip-hold portion and having a long product length as that in Patent Documents 1-3 is individually packaged (individually packaged) for portability, the absorbent article is preferably folded at fold lines that are provided at intervals in the longitudinal direction.

Patent Document 3 discloses providing three fold lines extending in a width direction of an absorbent article. In Patent Document 3, the positions of two fold lines closer to the ends of the absorbent article are defined in relation to positions at which the ends of elastic parts of three-dimensional gathers are fixed.

RELATED-ART DOCUMENTS

Patent Documents

[Patent Document 1] Japanese Patent No. 5082007
[Patent Document 2] Japanese Patent No. 3871611
[Patent Document 3] Japanese Patent No. 5947517

DISCLOSURE OF INVENTION

Problems to be Solved by the Invention

However, the rear flaps of the absorbent articles having shapes as described in Patent Documents 1-3 cannot flexibly deform along the round shape of a hip. Accordingly, the rear flaps may not fit the hip well.

Also, although Patent Document 3 discloses how to fold a long absorbent article, the positional relationship between the shape of a hip-hold portion and fold lines is not taken into account in the absorbent article of Patent Document 3.

The present invention is made in view of the above problems of the related-art technologies. An object of the present invention is to provide an individually-packaged absorbent article that can better fit a body and can prevent or reduce discomfort due to, for example, wrinkles formed in a hip-hold portion.

Means for Solving the Problems

To solve the above problems, a first embodiment of the present invention provides an individually-packaged absorbent article that includes an absorbent article including a body that includes a permeable upper-side sheet, an impermeable back-side sheet, and an absorbent disposed between the upper-side sheet and the back-side sheet, and a packaging sheet that individually packages the absorbent article. The body has a shape having a predetermined length in a longitudinal direction and a predetermined width in a direction orthogonal to the longitudinal direction. The absorbent article includes a hip-hold portion that includes a side area protruding from a rear side-edge of the body, and the side area includes a first protruding portion that includes a portion having a largest width from a longitudinal centerline of the body, a first recessed portion adjacent to a rear end of the first protruding portion, and a second recessed portion adjacent to a front end of the first protruding portion. The absorbent article is folded such that a mountain fold line is formed in the side area of the hip-hold portion, and the mountain fold line intersects with an edge of the side area of the hip-hold portion at a position between a first inflection point between the first recessed portion and the first protruding portion and a second inflection point between the first protruding portion and the second recessed portion, and is substantially orthogonal to the longitudinal centerline.

In the first embodiment, the side area of the hip-hold portion includes the first protruding portion including a portion having a largest width from the longitudinal centerline of the body, the first recessed portion adjacent to the rear end of the first protruding portion, and the second recessed portion adjacent to the front end of the first protruding portion.

With this configuration, when the hip-hold portion is brought into contact with the hip to wear the absorbent article, the first protruding portion can deform relatively independently without affecting the portions before and after the first protruding portion.

This deformation enables the hip-hold portion to flexibly deform along the curved shape (round shape) of the hip, and enables the hip-hold portion to better fit the body.

Also in the present embodiment, when the absorbent article is individually packaged, the absorbent article is folded such that a mountain fold line is formed in the side area of the hip-hold portion, and the mountain fold line intersects with an edge of the side area of the hip-hold portion at a position between the first inflection point between the first recessed portion and the first protruding portion and the second inflection point between the first protruding portion and the second recessed portion, and is substantially orthogonal to the longitudinal centerline.

The mountain fold line protrudes toward the hip, and the protrusion tends to initially contact the hip when the absorbent article is worn.

When the hip-hold portion is pressed against the hip, the protrusion is immediately pressed toward the underwear. As a result, areas on the sides of the mountain fold line are naturally pushed toward the first recessed portion and the second recessed portion that are adjacent to the areas.

This pushing causes the widest first protruding portion to be stretched in the longitudinal direction and thereby prevents formation of wrinkles in the first protruding portion.

This in turn makes it possible to improve the wear comfort of the absorbent article.

In the second embodiment of the present invention, the side area of the hip-hold portion is folded along a longitudinal fold line extending in the longitudinal direction; and each of an angle formed between the mountain fold line and a straight line that passes through an intersection point of an extension of the mountain fold line with the longitudinal fold line and a bottom point of the first recessed portion and an angle formed between the mountain fold line and a straight line that passes through the intersection point and a bottom point of the second recessed portion is between 30 degrees and 60 degrees.

According to the second embodiment, the mountain fold line in the side area of the hip-hold portion is formed in a predetermined position relative to the first recessed portion and the second recessed portion.

This configuration makes it possible to provide appropriate areas on the sides of the first protruding portion so that a wrinkle-forming force applied to the first protruding portion can be transferred to surrounding areas, and thereby makes it possible to reduce discomfort.

In a third embodiment of the present invention, a slip stopper for fixing the absorbent article is provided on the back-side sheet in the side area, and the slip stopper is disposed to cross the straight line passing through the intersection point and the bottom point of the second recessed portion.

According to the third embodiment, the slip stopper is disposed in a position near the bottom point of the second recessed portion.

With this configuration, even when stress is likely to excessively concentrate on the second recessed portion adjacent to the front end of the first protruding portion, the stress is distributed because an area near the second recessed portion is fixed to the underwear. Accordingly, this configuration makes it possible to prevent or reduce formation of large wrinkles.

A fourth embodiment of the present invention provides an absorbent article including a body that includes a permeable upper-side sheet, an impermeable back-side sheet, and an absorbent disposed between the upper-side sheet and the back-side sheet. The body has a shape having a predetermined length in a longitudinal direction and a predetermined width in a direction orthogonal to the longitudinal direction. The absorbent article further includes a hip-hold portion that includes a side area protruding from a rear side-edge of the body. The side area includes a first protruding portion that includes a portion having a largest width from a longitudinal centerline of the body, a first recessed portion adjacent to a rear end of the first protruding portion, and a second recessed portion adjacent to a front end of the first protruding portion. A mountain fold line is formed in the side area of the hip-hold portion. The mountain fold line intersects with an edge of the side area of the hip-hold portion at a position between a first inflection point between the first recessed portion and the first protruding portion and a second inflection point between the first protruding portion and the second recessed portion, and is substantially orthogonal to the longitudinal centerline.

The fourth embodiment can provide an absorbent article that has the same advantageous effects as those of the first embodiment described above.

Also, even when the absorbent article is individually packaged without being folded or multiple absorbent articles are stacked and packaged without being folded, the fourth embodiment can provide the same advantageous effects as those provided by the first embodiment.

A fifth embodiment of the present invention provides a method of folding an absorbent article. The absorbent article includes a body including a permeable upper-side sheet, an impermeable back-side sheet, and an absorbent disposed between the upper-side sheet and the back-side sheet. The body has a shape that has a predetermined length in a longitudinal direction and a predetermined width in a direction orthogonal to the longitudinal direction. The absorbent article also includes a hip-hold portion that includes a side area protruding from a rear side-edge of the body, and the side area includes a first protruding portion that includes a portion having a largest width from a longitudinal centerline of the body, a first recessed portion adjacent to a rear end of the first protruding portion, and a second recessed portion adjacent to a front end of the first protruding portion. The method includes folding the absorbent article such that a mountain fold line is formed in the side area of the hip-hold portion. The mountain fold line intersects with an edge of the side area of the hip-hold portion at a position between a first inflection point between the first recessed portion and the first protruding portion and a second inflection point between the first protruding portion and the second recessed portion, and is substantially orthogonal to the longitudinal centerline.

The fifth embodiment can provide a method of folding an absorbent article that has the same advantageous effects as those of the first embodiment described above.

Advantageous Effect of the Invention

An aspect of the present invention provides an individually-packaged absorbent article that can better fit a body and can prevent or reduce discomfort resulting from, for example, wrinkles formed in a hip-hold portion.

DESCRIPTION OF EMBODIMENTS

Embodiments of the present invention are described below with reference to the accompanying drawings.

<Absorbent Article>

Figure 1:
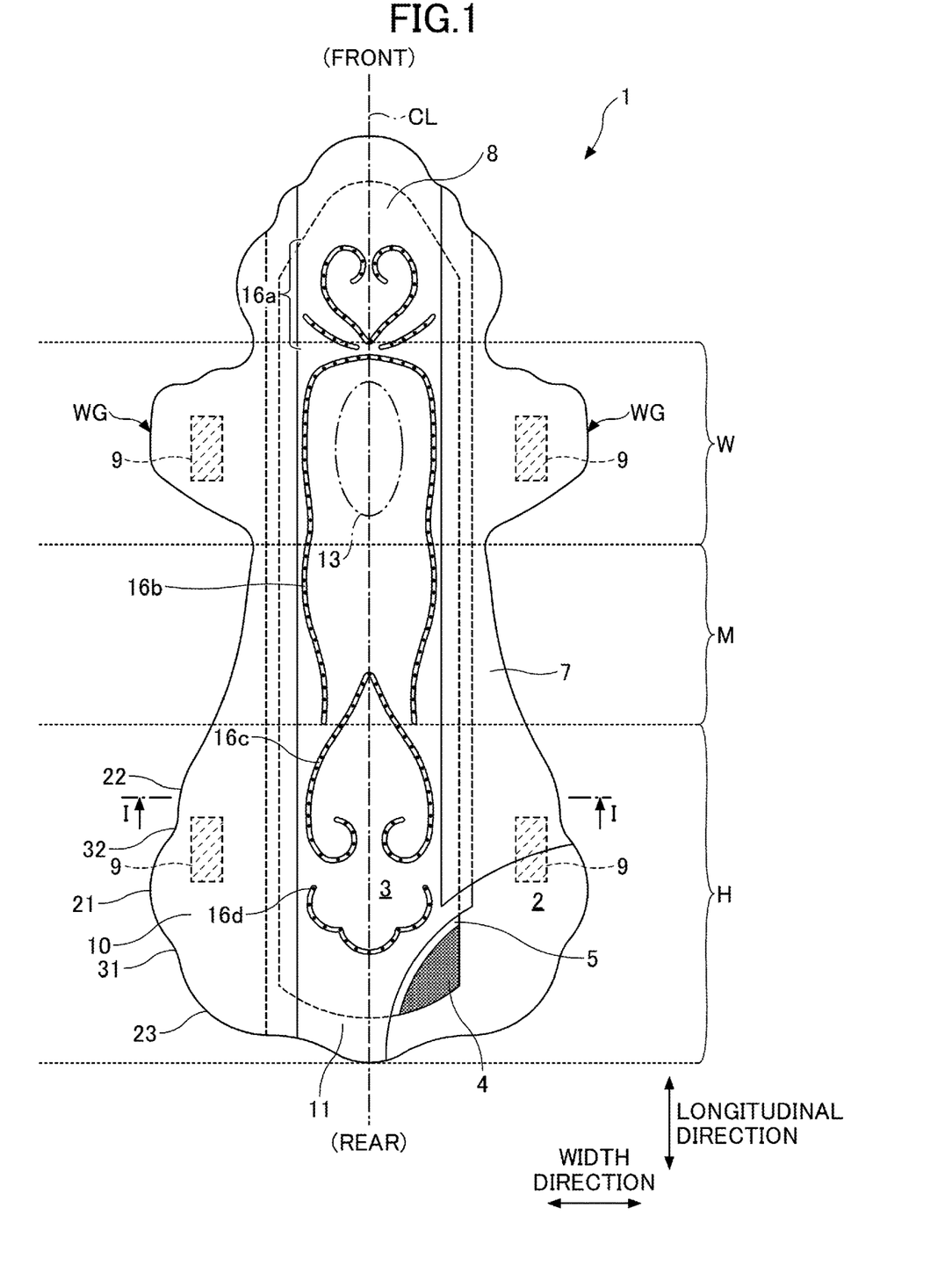
FIG. 1 is a partially-cutaway view of an absorbent article according to an embodiment of the present invention.
Figure 2:
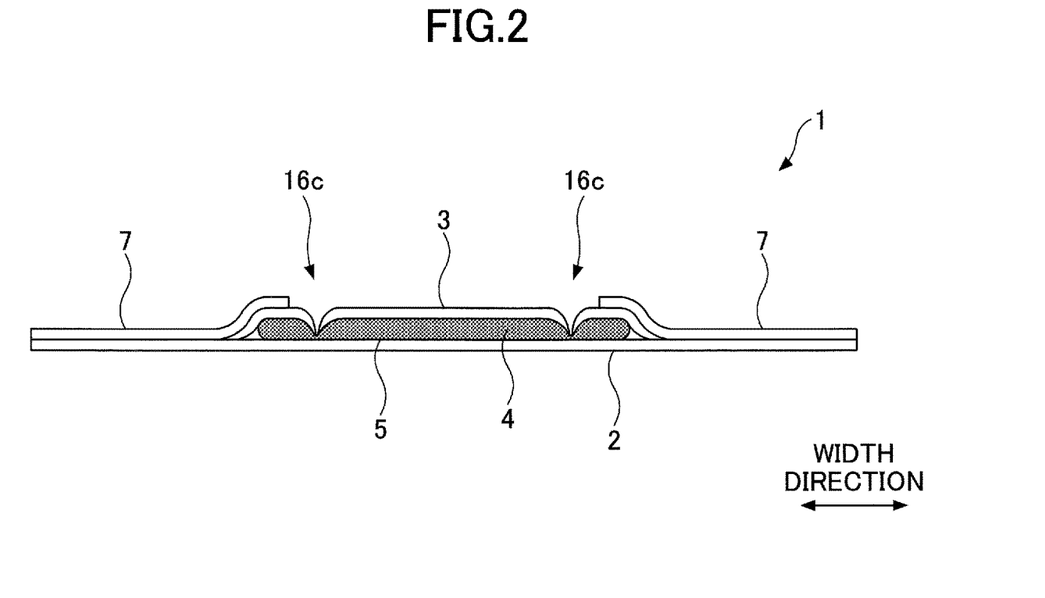
FIG. 2 is a cross-sectional view taken along line I-I of an absorbent article according to an embodiment of the present invention.

As illustrated in FIGS. 1 and 2, an absorbent article 1 includes a body (absorbent article body) 8 including an impermeable back-side sheet 2, a permeable upper-side sheet 3, and an absorbent 4 disposed between the sheets 2 and 3.

The absorbent 4 may be enveloped in an enveloping sheet 5 made of, for example, crepe paper or a nonwoven fabric to keep the shape of the absorbent 4.

As illustrated in FIG. 1, the absorbent article 1 also includes a hip-hold portion H, a wing portion W including wings WG, and a middle portion M disposed between the hip-hold portion H and the wing portion W.

The hip-hold portion H may extend from the rear end of a crotch of an underwear to the rear end of the absorbent article 1 when the absorbent article 1 is worn, and the wing portion W may be an area that extends from the front ends of the wings WG to the rear ends of the wings WG.

The absorbent article 1 is used by attaching the absorbent article 1 to underwear such that the wing portion W faces forward and the hip-hold portion H faces backward.

As illustrated in FIG. 1, the body 8 has an elongated shape having a predetermined length in the longitudinal direction and a substantially constant width in a direction orthogonal to the longitudinal direction.

The absorbent article 1 has a shape that is substantially axisymmetrical with respect to a centerline CL extending in the longitudinal direction.

At the front side edges and the rear side edges of the absorbent 4, the outer edges of the back-side sheet 2 and the outer edges of the upper-side sheet are bonded to each other by using, for example, an adhesive such as a hot melt, heat sealing, or ultrasonic sealing.

Also, side nonwoven fabrics 7 are provided on the sides of the upper-side sheet 3 along the longitudinal direction.

The side nonwoven fabrics 7 partially protrude from the body 8 in lateral directions and are stacked on the back-side sheet 2 also protruding in the lateral directions. The side nonwoven fabrics 7 are bonded to the back-side sheet 2 by using, for example, an adhesive such as a hot melt, heat sealing, or ultrasonic sealing and form side areas 10 of the hip-hold portion H and the wings WG.

The back-side sheet 2 may be implemented by an impermeable sheet material such as an olefin resin sheet formed of, for example, polyethylene or polypropylene.

Also, the back-side sheet 2 may be implemented by a laminated nonwoven fabric formed by stacking a nonwoven fabric on, for example, a polyethylene sheet, or a laminated sheet that is made substantially impermeable by stacking a waterproof film between nonwoven fabrics.

Further, a sheet having moisture permeability is more preferably used to prevent stuffiness.

As an impermeable and moisture-permeable sheet, a microporous sheet is preferably used. A microporous sheet is obtained by melt-mixing an inorganic filler with an olefin resin such as polyethylene or polypropylene to form a sheet, and by stretching the sheet uniaxially or biaxially.

The upper-side sheet 3 is a permeable sheet through which body fluids such as blood, discharge, and urine can permeate rapidly.

The upper-side sheet 3 is preferably formed of a porous or nonporous nonwoven fabric or a porous plastic sheet.

The nonwoven fabric may be formed by using one of or a combination of two or more of the following materials: olefins such as polyethylene and polypropylene, synthetic fibers such as polyester and polyamide, regenerated fibers such as rayon and cupra, a blend of these fibers, and natural fibers such as cotton.

The nonwoven fabric may be produced by, for example, spanlacing, spunbonding, thermal bonding, melt-blowing, or needle punching.

Among these production methods, spunlacing is preferable to produce a flexible nonwoven fabric, spunbonding is preferable to produce a nonwoven fabric with good draping characteristics, and thermal bonding is preferable to produce a bulky and soft nonwoven fabric.

Also, bicomponent fibers may be used for the nonwoven fabric. Examples of bicomponent fibers include a core-in-sheath fiber including a high-melting-point fiber as a core and a low-melting-point fiber as a sheath, a side-by-side fiber, and a split fiber.

The absorbent 4 disposed between the back-side sheet 2 and the upper-side sheet 3 preferably includes cotton pulp and an absorbent polymer, but may be formed of any material capable of absorbing and retaining body fluids.

A superabsorbent polymer (SAP) granular powder, a superabsorbent polymer fiber (SAF), or a combination of these materials may be used as the absorbent polymer.

Examples of the pulp include chemical pulp obtained from wood, cellulose fibers such as dissolving pulp, and artificial cellulose fibers such as rayon and acetate.

Hardwood and softwood may be used as the materials of the chemical pulp, but softwood is preferably used because of its long fiber length.

Synthetic fibers may also be added to the absorbent 4.

Examples of materials of the synthetic fibers include polyolefin such as polyethylene and polypropylene, polyester such as polyethylene terephthalate or polybutylene terephthalate, polyamide such as nylon, and a copolymer of these materials. Also, the synthetic fibers may be formed by mixing two or more of these materials.

Also, bicomponent fibers may be used for the synthetic fibers. Examples of bicomponent fibers include a core-in-sheath fiber including a high-melting-point fiber as a core and a low-melting-point fiber as a sheath, a side-by-side fiber, and a split fiber.

Further, a material obtained by surface-treating hydrophobic fibers with a hydrophilic agent to have an affinity to body fluids may be used as the synthetic fibers.

The thickness of the absorbent 4 is preferably between about 0.5 mm and 25 mm.

The absorbent 4 may not necessarily have a uniform thickness over its length and breadth, and a portion of the absorbent 4 corresponding to a body-fluid ejection part may have a swelling shape.

The absorbent 4 is preferably produced by fiber stacking or an air-laid method.

The side nonwoven fabrics 7 may be implemented by a water-repellent nonwoven fabric or a hydrophilically-treated nonwoven fabric.

For example, a water-repellent nonwoven fabric coated with a silicon-, paraffin-, or alkylchromic-chloride-repellent is preferably used to more effectively prevent penetration of body fluids such as blood and discharge or to improve the feel.

Also, a hydrophilically-treated nonwoven fabric is preferably used to improve the function of the hip-hold portion H for absorbing a body fluid such as blood.

As a type of the nonwoven fabric, an air-through nonwoven fabric, which is soft and unlikely to be creased and wrinkled, is preferably used.

Embossed portions where dot embossments or embossments with predetermined shapes are formed may be provided at predetermined positions on the outer edges of the side areas 10 of the hip-hold portion H and the wings WG of the wing portion W to join the side nonwoven fabrics 7 to the back-side sheet 2 and to increase the rigidity.

Compressed grooves (fit embossments) 16 may be formed on the body 8 to improve the contact between the absorbent article 1 and the user's body and to prevent leakage.

In the embodiment of FIG. 1, the compressed grooves 16 include a front compressed groove 16a that is mostly located closer to the front end than the wing portion W, a middle compressed groove 16b extending in the longitudinal direction to surround a body fluid ejection area 13, and a first rear compressed groove 16c and a second rear compressed groove 16d that are mostly located in the hip-hold portion H and correspond to an area from the gluteal cleft to the hip.

<Hip-Hold Portion>

The absorbent article 1 of the present embodiment includes the hip-hold portion H.

Figure 6:
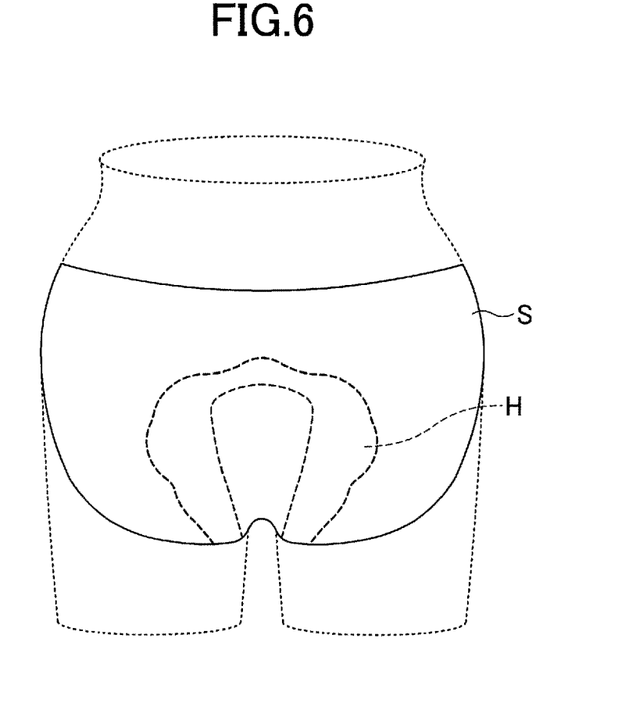
FIG. 6 is a drawing illustrating an absorbent article of an embodiment of the present invention that is worn on a body.

The hip-hold portion H is an area-expanded portion formed by increasing the length and width of rear side-portions and a rear-end portion of the absorbent article 1. As illustrated in FIG. 6, when the hip-hold portion H is attached to the inner surface of an underwear S at a position corresponding to the hip, the hip-hold portion H can prevent leakage of a body fluid from the absorbent article 1 in backward and/or obliquely-backward directions.

As illustrated in FIG. 1, the hip-hold portion H includes flap-like portions that are formed by stacking the side nonwoven fabrics 7 on the back-side sheet 2 and extend from rear side-portions to the rear end of the body 8 of the absorbent article 1.

The hip-hold portion H includes the side areas 10 protruding from the rear side-edges of the body 8 and a rear area 11 protruding from the rear end of the body 8.

The side areas 10 of the hip-hold portion H are composed mainly of areas formed by bonding the back-side sheet 2 to the side nonwoven fabrics 7, and the rear area 11 is composed mainly of an area formed by bonding the back-side sheet 2 to the upper-side sheet 3.

The side areas 10 and the rear area 11 of the hip-hold portion H preferably do not include the absorbent 4 and are preferably thinner than the body 8.

This configuration enables the side areas 10 and the rear area 11 to move more flexibly than the body 8.

Alternatively, an absorbent thinner than the absorbent 4 included in the body 8 may be provided between the back-side sheet 2 and the side nonwoven fabrics 7 in the hip-hold portion H.

The hip-hold portion H may extend from the rear end of a crotch of an underwear to the rear end of the absorbent article 1 when the absorbent article 1 is worn.

In the embodiment of FIG. 1, the hip-hold portion H extends in the longitudinal direction from the front end of a second protruding portion 22 located adjacent to the front end of a second recessed portion 32 to the rear end of the absorbent article 1.

For example, the length of the hip-hold portion H in the longitudinal direction is preferably between 5 cm and 20 cm and more preferably between 8 cm and 18 cm.

The total length of the absorbent article 1 may be greater than or equal to 27 cm, may be greater than or equal to 30 cm, and may be less than or equal to 45 cm.

The percentage of the length of the hip-hold portion H relative to the total length is preferably between 10% and 50%.

The hip-hold portion H may include a widest portion of the absorbent article 1, and the width of the widest portion is preferably between 12 cm and 23 cm.

<Outer Shape of Hip-Hold Portion>

The outline (contour) of the hip-hold portion H includes protrusions and recesses.

For example, as illustrated in FIG. 1, each of the side areas 10 of the hip-hold portion H includes a first protruding portion 21 including a portion having a largest width from the longitudinal centerline of the body 8, a first recessed portion 31 adjacent to the rear end of the first protruding portion 21, and a second recessed portion 32 adjacent to the front end of the first protruding portion 21.

The rear area 11 of the hip-hold portion H protruding from the rear end of the body 8 may also include protruding portions and recessed portions as illustrated in FIG. 1.

Below, an effect of forming protrusions and recesses in the outline of the hip-hold portion H is described.

The hip-hold portion H has a substantially planar shape.

When the planar hip-hold portion H is brought into contact with the hip, the peripheral areas (the side areas 10 and the rear area 11) of the hip-hold portion H may be distorted and wrinkled due to the difference between the planar shape of the hip-hold portion H and the curved surface shape of the hip.

The size and number of wrinkles to be formed depend on the total area of the hip-hold portion H and the shapes of curved surfaces of the hip. If the protrusions and recesses described above are not formed in the outline of the hip-hold portion H, wrinkles and twists may be formed at multiple positions in the peripheral areas of the hip-hold portion H.

If such wrinkles contact the skin of the hip, the user may feel uncomfortable. Particularly, when the user is sitting on a chair for a long time or lying on the back at night, a part of the body weight is applied to the hip, and the uncomfortableness or the discomfort increases.

Also, when the body weight applied to the hip or the state of contact between the hip and the hip-hold portion H changes due to changes in the posture of the user during sleep or changes in the posture of the user sitting on a chair, the size of wrinkles may further increase.

Further, when the user is sleeping on the back or side at night, body fluids are more likely to leak through a gap formed by the wrinkles.

In the present embodiment, the first protruding portion 21 and the first and second recessed portions 31 and 32 located adjacent to the ends of the first protruding portion 21 are formed in the hip-hold portion H. With this configuration, even if a force that causes wrinkles is applied to the first protruding portion 21, the force is not transmitted to the entire hip-hold portion H and is only transmitted up to the first recessed portion 31 and the second recessed portion 32 where stress tends to concentrate.

Accordingly, this configuration makes it possible to prevent wrinkles from extending into the area of the middle portion M that is close to a part around the leg where wrinkles particularly cause discomfort.

That is, the first protruding portion 21 can deform independently without significantly affecting portions adjacent to the first protruding portion 21.

Accordingly, when the hip-hold portion H is brought into contact with the curved surface of the hip to wear the absorbent article, the hip-hold portion H can be deformed along the curved surface of the hip.

This also improves the fit of the hip-hold portion H to the hip.

The radii of curvature (in " "mm") of the first protruding portion 21, the first recessed portion 31, and the second recessed portion 32 formed in the side areas 10 of the hip-hold portion H are selected appropriately according to the shapes and sizes of the body 8 and the hip-hold portion H and are not limited to specific values.

For example, the radius of curvature of the first protruding portion 21 may be 25-35 mm, the radius of curvature of the first recessed portion 31 may be 15-mm, and the radius of curvature of the second recessed portion 32 may be 10-20 mm.

Also, when the second protruding portion 22 is formed adjacent to the front end of the second recessed portion 32, the radius of curvature of the second protruding portion 22 may be 36-46 mm.

When a third protruding portion 23 is formed adjacent to the rear end of the first recessed portion 31, the radius of curvature of the third protruding portion 23 may be 30-40 mm.

In the present embodiment, the first protruding portion 21, the first recessed portion 31, and the second recessed portion 32 are formed in each of the side areas 10 of the hip-hold portion H. In the example of FIG. 1, the second protruding portion 22 adjacent to the front end of the second recessed portion 32 and the third protruding portion 23 adjacent to the rear end of the first recessed portion 31 are also formed.

However, the number and shapes of protruding portions and recessed portions are not limited those illustrated in FIG. 1.

For example, one through five protruding portions and two through five recessed portions may be formed in each of the side areas 10 of the hip-hold portion H.

<Individually-Packaged Absorbent Article>

The present embodiment is related to an individually-packaged absorbent article, i.e., the absorbent article 1 that is individually packaged to be able to be conveniently and hygienically carried.

The individually-packaged absorbent article includes the absorbent article 1 and a packaging sheet 18.

The packaging sheet 18 preferably has a shape that can wrap the absorbent article 1.

For example, the packaging sheet 18 may have a rectangular shape in plan view as illustrated in FIGS. 5A through 5E.

Alternatively, the packaging sheet 18 may have a square shape in plan view.

The packaging sheet 18 may be formed of, for example, a polyolefin film formed of polypropylene or polyethylene, a film formed of polyester or polyvinyl alcohol, a nonwoven fabric, or a laminated nonwoven fabric (such as a polyethylene-laminated nonwoven fabric).

When weight is given to printed designs, a film is preferably used; and when weight is given to the texture and softness, a nonwoven fabric is preferably used.

The absorbent article is individually packaged after being folded. The absorbent article is preferably folded in three or more and is more preferably folded in four or more, along fold lines that are substantially orthogonal to the longitudinal direction.

Folding the absorbent article in four or more (with three or more fold lines) makes it possible to provide a compact product that can be easily carried and stored even if the absorbent article is long.

In addition to folding the absorbent article along fold lines that are substantially orthogonal to the longitudinal direction, the side areas 10 of the hip-hold portion H and the wings WG are preferably folded inward along the side edges of the body 8.

That is, the side areas 10 and the wings WG are preferably folded along fold lines L0 (FIG. 5A) extending in the longitudinal direction.

Folding the side expanded portions makes it easier to carry the individually-packaged absorbent article.

The side areas 10 of the hip-hold portion H and the wings WG are thin flap-shaped portions. Therefore, the side areas 10 and the wings WG are preferably folded along the longitudinal direction before the absorbent article is folded along fold lines substantially orthogonal to the longitudinal direction so that formation of unnecessary wrinkles in the side areas 10 and the wings WG can be reduced.

<Mountain Fold Lines>

The absorbent article 1 of the present embodiment is folded such that a mountain fold line Y is formed in the side areas 10 of the hip-hold portion H.

Figure 3:
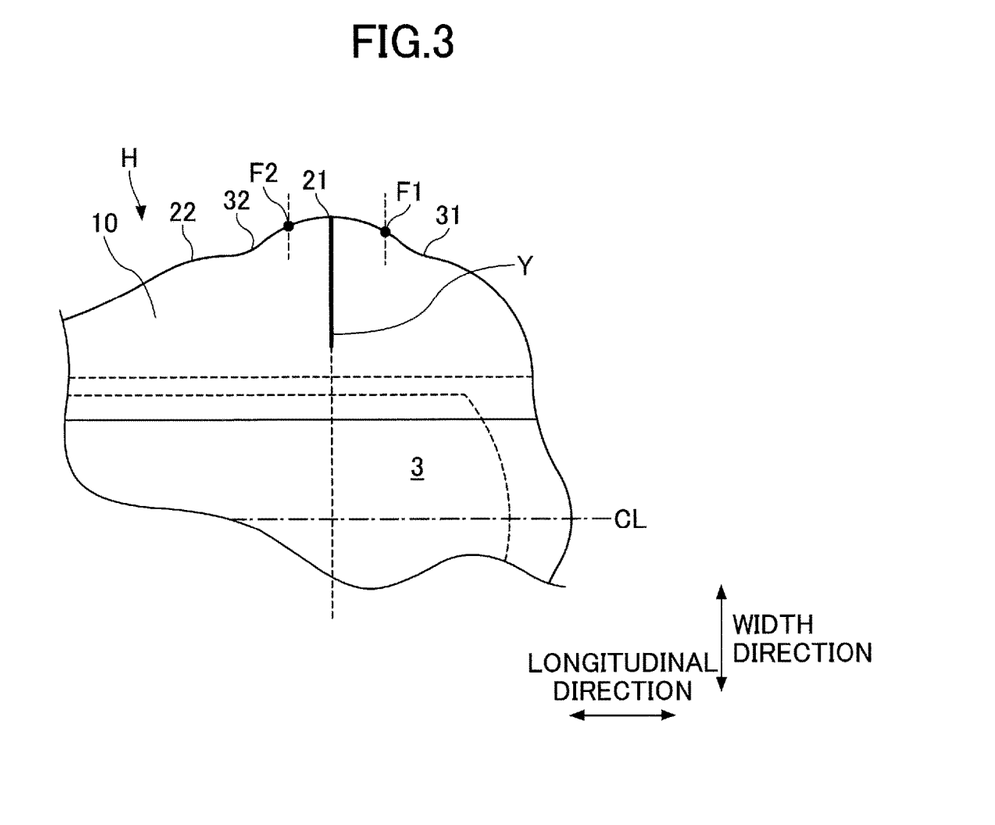
FIG. 3 is an enlarged view of a part of a side area of a hip-hold portion according to an embodiment of the present invention.

FIG. 3 is an enlarged view of a part of one of the side areas 10 of the hip-hold portion H.

As illustrated in FIG. 3, the mountain fold line Y intersects with an edge of the side area 10 of the hip-hold portion H at a position between a first inflection point F1 between the first recessed portion and the first protruding portion 21 and a second inflection point F2 between the first protruding portion 21 and the second recessed portion 32 and is substantially orthogonal to the longitudinal centerline CL.

That is, the fold line Y formed in the hip-hold portion H intersects with the edge of the widest first protruding portion 21 at a position near the peak of the first protruding portion 21 and is substantially orthogonal to the longitudinal centerline CL.

Here, a mountain fold line is a line that is formed by folding the absorbent article 1 such that the upper side (the side on which the upper-side sheet 3 is provided) of the absorbent article 1 protrudes upward to form a mountain-like shape.

Also, "substantially orthogonal to the longitudinal centerline CL" does not necessarily indicate that the fold line Y is exactly orthogonal to the longitudinal centerline CL. For example, the fold line Y may form an angle of ±15 degrees with the longitudinal centerline CL and may preferably form an angle of ±5 degrees with the longitudinal centerline CL.

The mountain fold line Y is preferably formed at a distance of less than or equal to 15 mm, is more preferably formed at a distance of less than or equal to 8 mm, and is further preferably formed at a distance of less than or equal to 5 mm, from the peak of the first protruding portion 21 in the forward or backward direction.

Also, the mountain fold line Y is more preferably a line that passes through the peak of the first protruding portion 21 and is orthogonal to the longitudinal centerline CL.

Further, the mountain fold line Y may extend to a position near the side edge of the body 8, and may preferably extend to the closest longitudinal fold line L0 or to the side edge of the body 8.

Generally, when an absorbent article is worn, wrinkles and twists (which may be hereafter simply referred to as wrinkles) tend to be randomly formed (with irregular depths and lengths) in the side areas 10 and the rear area 11 of the hip-hold portion H.

This tendency is especially prominent in the first protruding portion 21 that is a widest part in the side area 10.

When the wrinkles in the first protruding portion 21 contact the skin, the wrinkles may cause discomfort.

In the present embodiment, the absorbent article 1 is folded such that the mountain fold line Y is formed near the first protruding portion 21 of the side area 10 of the hip-hold portion H.

The mountain fold line Y is maintained, i.e., the fold at the mountain fold line Y is protruding on the side of the upper-side sheet 3, even when the package is opened to use the absorbent article 1.

Therefore, when the absorbent article 1 is worn, the protruding portion along the mountain fold line Y protrudes toward the hip and contacts the skin first.

When the hip-hold portion H is set along the hip, the protruding portion along the mountain fold line Y is immediately pressed toward the underwear by a force of the hip.

As a result, areas on the opposite sides of the mountain fold line Y are naturally pushed toward the adjacent first and second recessed portions 31 and 32.

When the areas on the opposite sides of the mountain fold line Y are pushed as described above, the first protruding portion 21, which is most likely to move and where wrinkles are most likely to be formed among parts of the hip-hold portion H, is smoothly stretched in the longitudinal direction.

This in turn makes it possible to prevent formation of wrinkles in the first protruding portion 21.

As described above, because the first protruding portion 21 is the widest area in the absorbent article 1, irregular wrinkles formed in the first protruding portion 21 may directly cause discomfort.

The present embodiment can suppress formation of wrinkles in the first protruding portion 21 with a large area and thereby improve the wear comfort of the absorbent article 1.

Also, even when a large force is applied to the side areas 10 of the hip-hold portion H and formation of wrinkles cannot be prevented, the wrinkles are mainly formed in recessed portions such as the first recessed portion 31 and the second recessed portion 32 were stress tends to concentrate.

Because the length of a recessed portion in the width direction is less than the length of a protruding portion in the width direction, the length of wrinkles formed in the recessed portion is less than the length of wrinkles formed in the protruding portion. Therefore, the discomfort caused by the wrinkles formed in the recessed portion is less than the discomfort caused by the wrinkles formed in the protruding portion with a greater width.

As described above, in the individually-packaged absorbent article of the present embodiment, protrusions and recesses are formed in the side areas 10 of the hip-hold portion H, and the absorbent article is folded such that the mountain fold line Y is formed near the first protruding portion 21. This configuration enables the absorbent article to better fit the body and makes it possible to effectively prevent or reduce discomfort.

The mountain fold line Y may or may not extend continuously from the peak of the first protruding portion 21 to the side edge of the body 8.

For example, as illustrated in FIG. 3, the mountain fold line Y may extend from a position near the peak of the first protruding portion 21 to the middle of the first protruding portion 21.

Multiple mountain fold lines Y may be formed when the mountain fold lines Y intersect with the edge of the side area 10 of the hip-hold portion H at positions between the first inflection point F1 and the second inflection point F2 and are substantially orthogonal to the longitudinal centerline CL. However, if a large number of mountain fold lines Y are provided, the mountain fold lines Y themselves cause discomfort and may reduce the effect of reducing discomfort by stretching randomly formed wrinkles toward surrounding areas. Therefore, the number of mountain fold lines Y is preferably one and is less than or equal to three at a maximum.

The side areas 10 of the hip-hold portion H are preferably folded along the longitudinal fold lines L0 (FIG. 5A) as described above.

The positional relationship between the mountain fold line Y and the first and second recessed portions 31 and 32 is described below with reference to FIG. 4 that is an enlarged view of a part of one of the side areas 10 of the hip-hold portion H.

Figure 4:
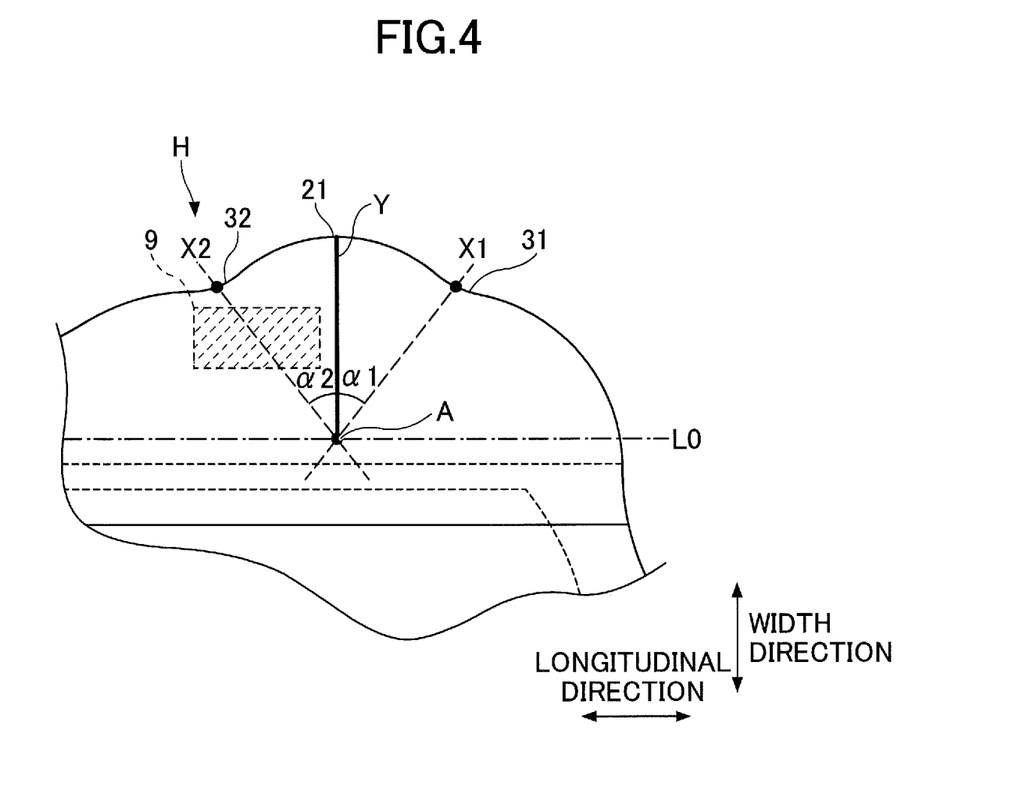
FIG. 4 is an enlarged view of a part of a side area of a hip-hold portion according to an embodiment of the present invention.

As illustrated in FIG. 4, an angle $\alpha 1$ formed between the mountain fold line Y (or its extension) and a straight line X1, which passes through an intersection point A of the mountain fold line Y (or its extension) with the longitudinal fold line L0 and a bottom point of the first recessed portion 31, is preferably between 30 and 60 degrees and more preferably between 35 and 45 degrees.

Similarly, an angle $\alpha 2$ formed between the mountain fold line Y and a straight line X2, which passes through the intersection point A and a bottom point of the second recessed portion 32, is preferably between 30 and 60 degrees and more preferably between 35 and 45 degrees.

In the present application, the bottom point of the first recessed portion 31 is a point at the bottom of a recess between the first protruding portion 21 and the third protruding portion 23 that are adjacent to the first recessed portion 31. When a line contacting both the first protruding portion 21 and the third protruding portion 23 (a line passing through the peak of the first protruding portion 21 and the peak of the third protruding portion 23) is drawn and a normal line is drawn from the line to the first recessed portion 31, the bottom point of the first recessed portion 31 corresponds to a position at which the length of the normal line becomes longest.

The bottom point of the second recessed portion 32 is a point at the bottom of a recess between the first protruding portion 21 and the second protruding portion 22 that are adjacent to the second recessed portion 32. When a line contacting both the first protruding portion 21 and the second protruding portion 22 (a line passing through the peak of the first protruding portion 21 and the peak of the second protruding portion 22) is drawn and a normal line is drawn from the line to the second recessed portion 32, the bottom point of the second recessed portion 32 corresponds to a position at which the length of the normal line becomes longest.

Setting the relationship between the position of the mountain fold line Y and the position of the first recessed portion 31 and the relationship between the position of the mountain fold line Y and the position of the second recessed portion 32 to satisfy the conditions described above makes it possible to provide appropriate areas on the sides of the first protruding portion 21 so that a wrinkle-forming force applied to the first protruding portion 21 can be transferred to surrounding areas.

That is, setting the angles α1 and α2 at values greater than or equal to 30 degrees makes it possible to prevent wrinkles from being formed at a position near the first protruding portion 21 and increasing discomfort. Also, setting the angles α1 and α2 at values less than or equal to 60 degrees makes it possible to concentrate wrinkles in recessed portions even when the wrinkles are formed due to excessive concentration of stress.

The angles α1 and α2 may be the same or different from each other.

When the user is sitting on a chair, for example, the hip tends to move relative to the hip-hold portion H from a backward position to a forward position, and the skin tends to contact the hip-hold portion H at a position near the front end of the first protruding portion 21.

Even in such a case, if the angle α2 is greater than the angle α1, a wider area in front of the first protruding portion 21 is stretched. As a result, formation of irregular wrinkles can be prevented, and discomfort can be reduced.

<Slip Stopper>

As illustrated in FIGS. 1 and 4, slip stoppers 9 are provided on the back-side sheet 2 of the hip-hold portion H to fix the absorbent article 1.

The slip stoppers 9 are adhesive or non-adhesive layers. The hip-hold portion H is attached via the slip stoppers 9 to the underwear to prevent the hip-hold portion H from moving from a predetermined position on the underwear.

The slip stoppers 9 may be implemented by adhesive or non-adhesive layers.

For example, the adhesive layers may be composed essentially of a styrene polymer, a tackifier, a plasticizer, or a combination of them.

Examples of the tackifier and the plasticizer include ester polymers and various types of petroleum resins that are solid at ambient temperature.

The non-adhesive layers may be implemented by an elastomer such as rubber.

In the present embodiment, as illustrated in FIG. 4, the slip stopper 9 may be disposed in a position near the bottom point of the second recessed portion 32.

The slip stopper 9 is preferably disposed to extend across the straight line X2 passing through the intersection point A of the mountain fold line Y (or its extension) with the longitudinal fold line L0 and the bottom point of the second recessed portion 32.

With this configuration, even when stress excessively concentrates on an area near the second recessed portion 32, the stress is distributed because the area near the second recessed portion 32 is fixed to the underwear. Accordingly, this configuration makes it possible to prevent or reduce formation of wrinkles or formation of large wrinkles.

Also, because the slip stopper 9 is formed near the second recessed portion 32 that is relatively close to an area around the leg, the slip stopper 9 can prevent formation of wrinkles and twists in the area around the leg where discomfort tends to be particularly felt and can maintain the wear comfort of the absorbent article 1.

In the present embodiment, the radius of curvature of the first protruding portion 21 is preferably greater than the radius of curvature of the first recessed portion 31 and the radius of curvature of the second recessed portion 32.

That is, indentations at the first recessed portion 31 and the second recessed portion 32 are preferably deep.

This facilitates formation of the mountain fold line Y in the first protruding portion 21 when the absorbent article is folded.

With this configuration, even when a force causing wrinkles and twists is applied to the first protruding portion 21, the wrinkles and twists can be effectively transferred to areas adjacent to the first protruding portion 21, i.e., to the first recessed portion 31 and the second recessed portion 32.

<Method of Folding Absorbent Article>

A method of folding the absorbent article 1 is described in detail below.

In the present embodiment, as illustrated in FIGS. 5A through 5E, the absorbent article 1 is folded in four in the longitudinal direction of the absorbent article 1 together with the packaging sheet 18 and a release sheet 19.

Folding the absorbent article 1 in four makes it easier to carry the absorbent articles 1 even if its size is large.

However, depending on the size and use of the absorbent article 1, the absorbent article 1 may be folded in three.

Figure 5A:
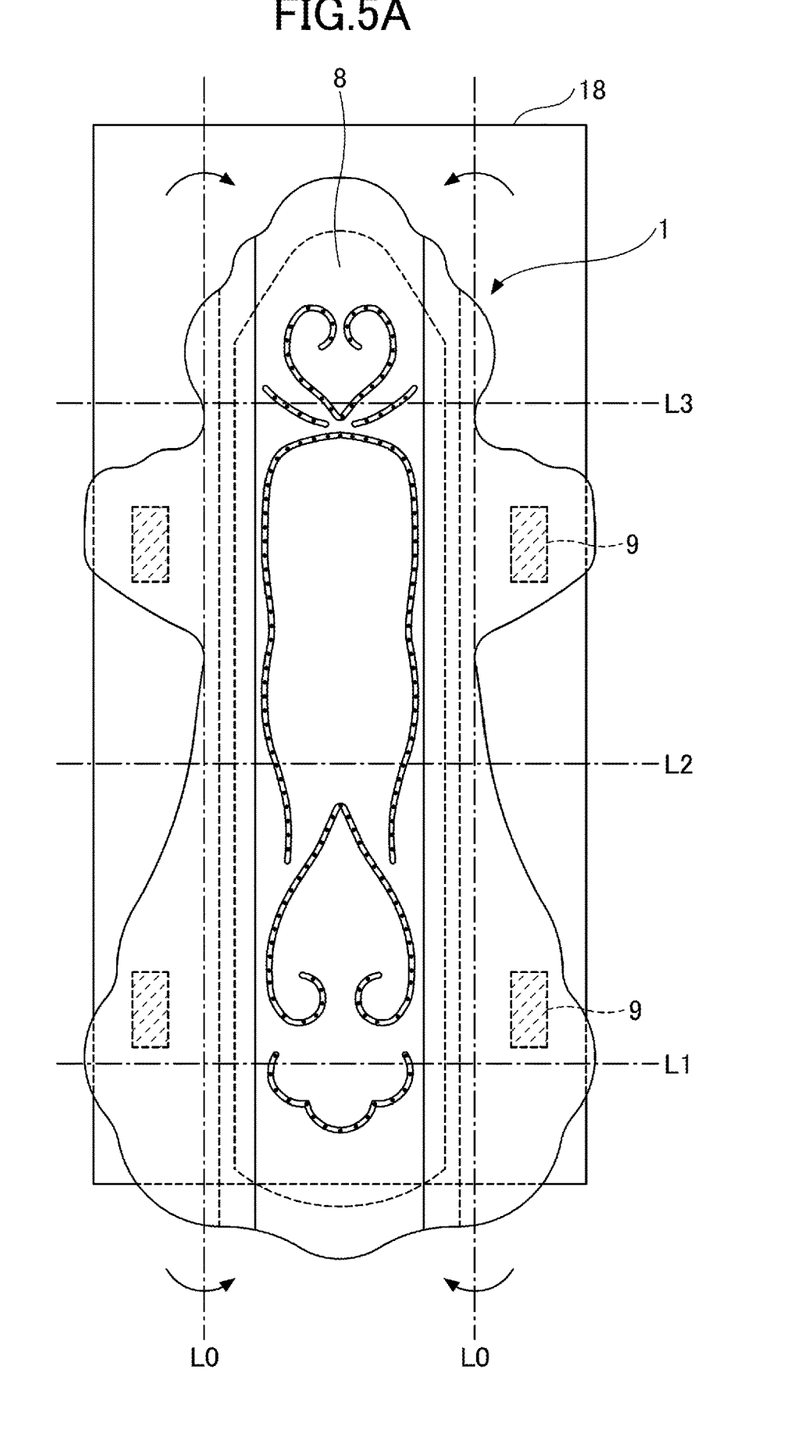
FIG. 5A is a drawing illustrating a process of individually-packaging an absorbent article according to an embodiment of the present invention.

In a folding process, the absorbent article 1 is first placed on the packaging sheet 18 as illustrated in FIG. 5A.

The packaging sheet 18 preferably has a width that is substantially equal to or greater than a larger one of the maximum width of the hip-hold portion H and the maximum width of the wing portion W.

Also, as illustrated in FIG. 5A, the length of the packaging sheet 18 in the longitudinal direction may not necessarily be greater than the length of the absorbent article 1 in the longitudinal direction.

Even in this case, the absorbent article 1 is preferably placed on the packaging sheet 18 such that the front end of the packaging sheet 18 is located ahead of the front end of the absorbent article 1.

Next, as indicated by arrows in FIG. 5A, flap-like portions extending outward from the side edges of the body 8, i.e., the side areas 10 of the hip-hold portion H and the wings WG, are folded inward (toward the upper-side sheet 3) along the longitudinal fold lines L0.

As a result of folding the side areas 10 and the wings WG inward, valley fold lines are formed in the longitudinal direction along the side edges of the body 8. Accordingly, when the absorbent article 1 is taken out of the package and worn, the side areas 10 of the hip-hold portion H form a shape to cover the hip. Thus, this configuration enables the absorbent article 1 to better fit the hip.

When the side areas 10 and the wings WG are folded, the slip stoppers 9 on the back-side sheet 2 appear on the upper side. To maintain the adhesion of the slip stoppers 9, the release sheet 19 is placed on the slip stoppers 9.

Figure 5B:
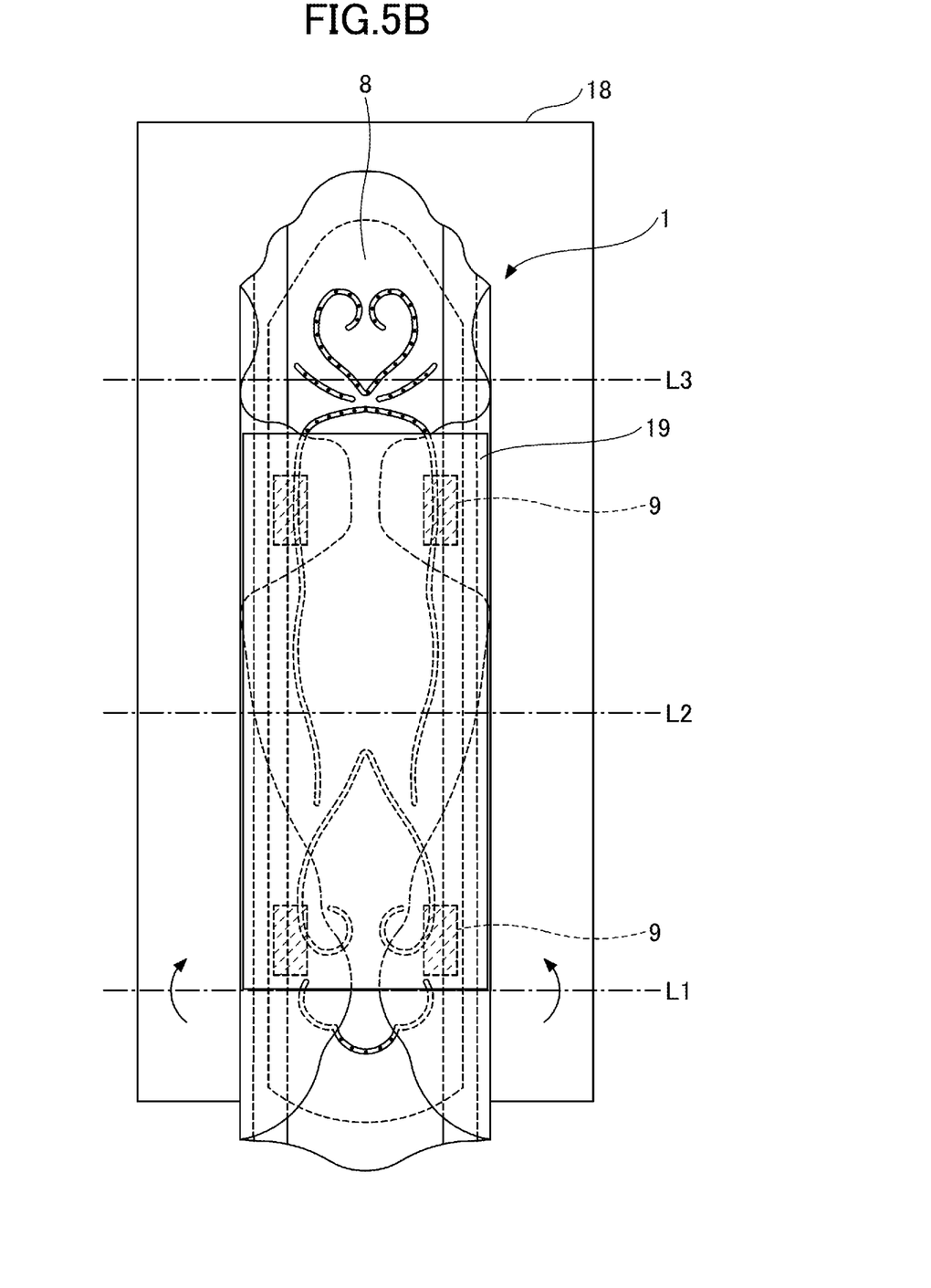
FIG. 5B is a drawing illustrating a process of individually-packaging an absorbent article according to an embodiment of the present invention.

FIG. 5B illustrates a state after the release sheet 19 is placed.

The release sheet 19 may have a rectangular shape as illustrated in FIG. 5B. However, the shape of the release sheet 19 is not limited to the rectangular shape and may instead be, for example, an oval shape as long as the release sheet 19 can be placed to cover the slip stoppers 9 during the folding process.

Also, multiple release sheets 19 may be provided to respectively cover the slip stoppers 9 on the wings WG and the side areas 10 of the hip-hold portion H.

The release sheet 19 may be implemented by, for example, paper, a polyolefin film formed of polypropylene or polyethylene, a film formed of polyester or polyvinyl alcohol, a nonwoven fabric, or a laminated nonwoven fabric (such as a polyethylene-laminated nonwoven fabric) including a contact surface that contacts the slip stoppers 9 and on which a release treatment is performed.

The release treatment may be performed by applying or spraying a release treatment liquid such as a silicone resin, a fluorine resin, or a tetrafluoroethylene resin onto the contact surface.

Also, any film or nonwoven fabric on which no release treatment is performed may be used as the release sheet 19 as long as it can be easily removed from the slip stoppers 9 and does not decrease the adhesion of the slip stoppers 9.

Figure 5C:
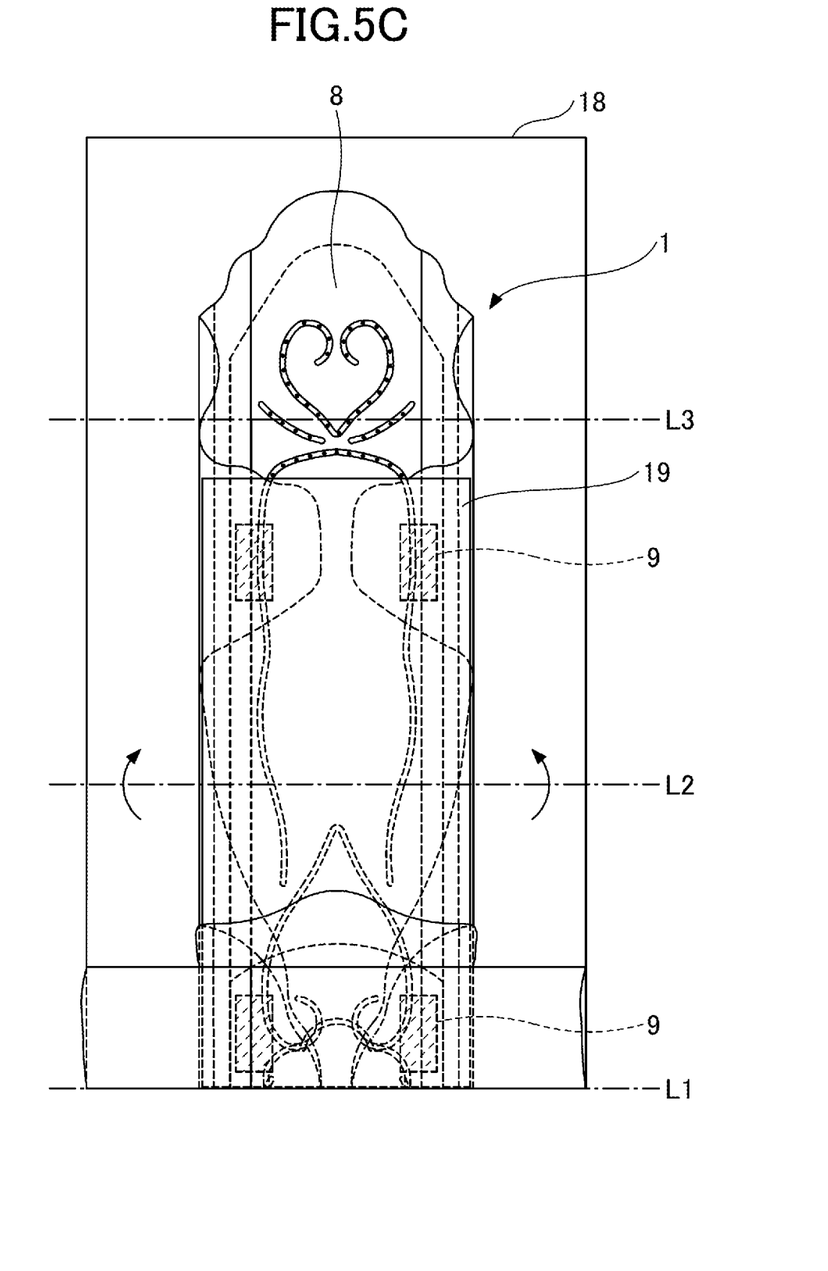
FIG. 5C is a drawing illustrating a process of individually-packaging an absorbent article according to an embodiment of the present invention.

After the release sheet 19 is placed, the absorbent article 1 is folded along a first fold line L1 together with the packaging sheet 18 from the side of the hip-hold portion H.

FIG. 5C illustrates a state after the absorbent article 1 is folded along the first fold line L1.

As a result of folding the absorbent article 1 along the first fold line L1, the mountain fold line Y is firmed in each side area 10 of the hip-hold portion H. As described above, the mountain fold line Y intersects with an edge of the side area 10 of the hip-hold portion H at a position between the first inflection point between the first recessed portion 31 and the first protruding portion 21 and the second inflection point between the first protruding portion 21 and the second recessed portion 32 and is substantially orthogonal to the longitudinal centerline CL.

The mountain fold line Y is preferably formed to pass through the peak of the first protruding portion 21 and to extend in a direction that is orthogonal to the longitudinal centerline CL.

Figure 5D:
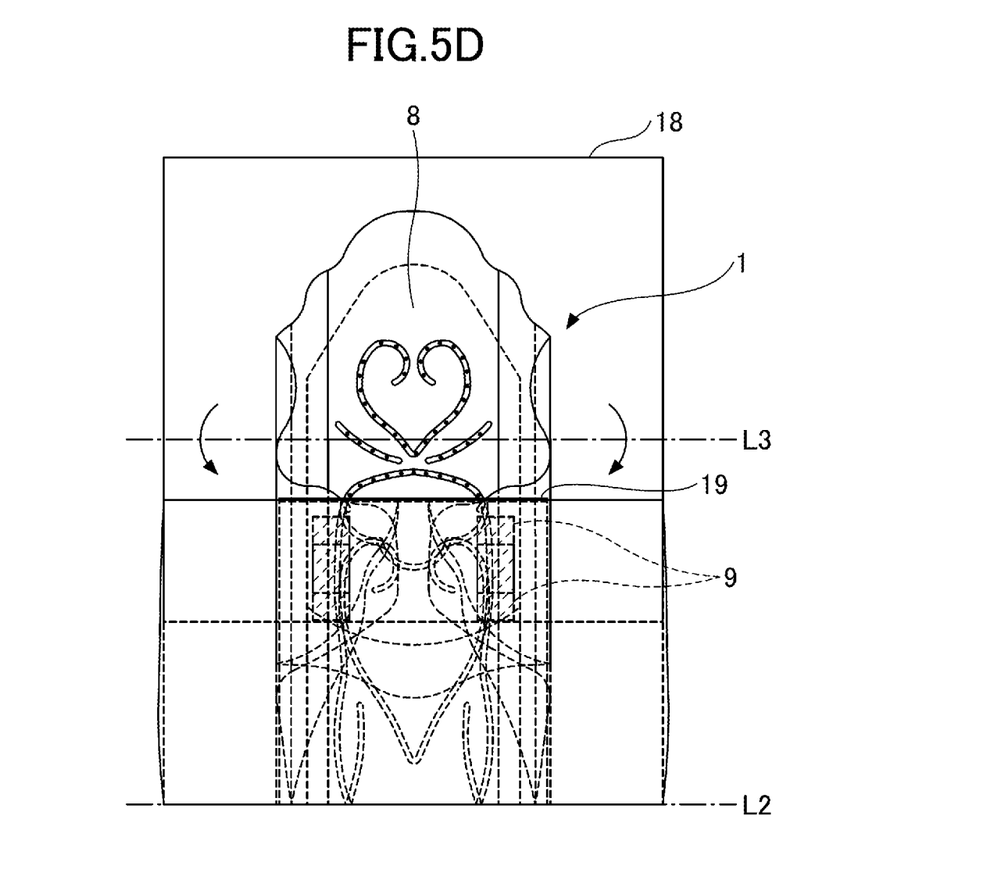
FIG. 5D is a drawing illustrating a process of individually-packaging an absorbent article according to an embodiment of the present invention.

Next, the absorbent article 1 is folded inward from the rear side together with the packaging sheet 18 along a second fold line L2 located ahead of the first fold line L1.

FIG. 5D illustrates a state after the absorbent article 1 is folded along the second fold line L2.

The second fold line L2 is formed to cross the middle portion M located behind the wing portion W in the width direction, and is preferably formed in an area other than the body fluid ejection area 13 (FIG. 1) so that the absorption performance of the body fluid ejection area 13 is not decreased as a result of bending the absorbent article 1.

Also, the second fold line L2 is preferably formed ahead of the first rear compressed groove 16c (FIG. 1) of the compressed grooves 16, which corresponds to an area from the gluteal cleft to the hip, to prevent bending the first rear compressed groove 16c and degrading its function.

After being folded along the second fold line L2, the absorbent article 1 is folded from the front side (from the upper side in FIG. 5D) as indicated by arrows in FIG. 5D along a third fold line L3 ahead of the second fold line L2.

The third fold line L3 is preferably located ahead of the wing portion W to prevent formation of wrinkles in the wings WG.

Figure 5E:
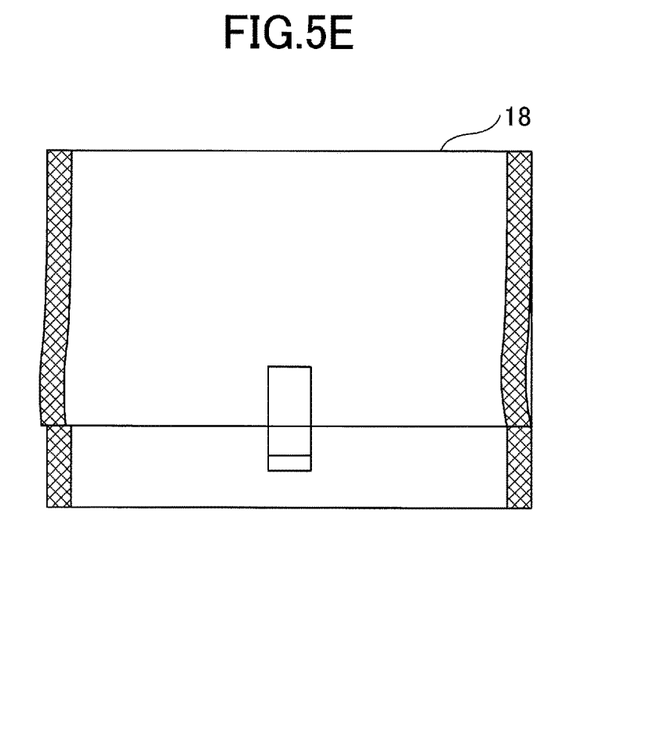
FIG. 5E is a drawing illustrating a process of individually-packaging an absorbent article according to an embodiment of the present invention.

FIG. 5E illustrates the individually-packaged absorbent article obtained by folding the absorbent article 1 along the third fold line L3.

After the absorbent article 1 is folded along the third fold line L3, the ends of the packaging sheet may be joined by using, for example, embossing, thermal bonding, or an adhesive.

Also, the front end of the packaging sheet 18 of the individually-packaged absorbent article may be fixed using, for example, a sealing tape, embossing, thermal bonding, or an adhesive to prevent the front end of the packaging sheet 18 from opening.

In the present embodiment, the entire absorbent article 1 is folded in the longitudinal direction after folding the side areas 10 of the hip-hold portion H and the wings WG of the wing portion W inward as indicated by the arrows in FIG. 5A.

Alternatively, in the initial step, the side areas 10 of the hip-hold portion H and the wings WG of the wing portion W may be folded in directions that are opposite the directions indicated by the arrows in FIG. 5A. That is, the side edges of the body 8 may be folded outward (toward the back-side sheet 2) along the longitudinal direction.

Even when the side edges are folded outward, the mountain fold lines Y can be formed in the side areas 10 of the hip-hold portion H by folding the absorbent article 1 in the longitudinal direction such that the upper-side sheet 3 faces inward.

The first fold line L1 may be located at a distance between 30 mm and 200 mm from the rear end of the absorbent article 1.

The second fold line L2 is preferably located at a distance between 120 mm and 350 mm from the rear end of the absorbent article 1.

The third fold line L3 is preferably located at a distance between 50 mm and 100 mm from the front end of the absorbent article 1.

In the embodiment illustrated by the figures, the slip stoppers 9 are provided beforehand on the back-side sheet 2 of the absorbent article 1, and the release sheet 19 is provided to cover the slip stoppers 9. However, the slip stoppers 9 may be provided on the release sheet 19 instead of on the absorbent article 1.

That is, the slip stoppers 9 may be provided on the release sheet 19 such that when the release sheet 19 is placed on the absorbent article 1 that is folded inward along the longitudinal fold lines L0, the slip stoppers 9 face the desired positions on the wings WG and the side areas 10 of the hip-hold portion H of the absorbent article 1.

Then, the release sheet 19 with the slip stoppers 9 is placed on the absorbent article 1 folded inward along the longitudinal fold lines L0 such that the surface of the release sheet 19 on which the slip stoppers 9 are provided faces the absorbent article 1. Even in this case, similarly to the above embodiment, the absorbent article 1 can be folded along the first fold line L1, the second fold line L2, and the third fold line L3 in this order.

When the slip stoppers 9 are provided beforehand on the release sheet 19 as described above, an adhesive may be applied to the surfaces of the slip stoppers 9 facing the absorbent article 1 so that the slip stoppers 9 can be fixed to the back-side sheet 2 of the absorbent article 1.

In the above embodiment, the mountain fold line Y is formed when the absorbent article 1 is folded for packaging. Alternatively, the mountain fold line Y may be formed in advance in the absorbent article 1.

In this case, the mountain fold line Y may be formed by, for example, a folding process or a compression process.

For example, in the state as illustrated in FIG. 5A where the absorbent article 1 is spread out, the mountain fold lines Y can be formed at least in the side areas 10 of the hip-hold portion H.

When the mountain fold lines Y are formed in advance, the absorbent article 1 may be individually packaged in the state illustrated in FIG. 5B without folding the absorbent article 1 in the longitudinal direction.

That is, the absorbent article 1 may be individually packaged in a state where the flap-like portions extending outward from the side edges of the body 8, i.e., the side areas 10 of the hip-hold portion H and the wings WG, are folded inward.

In this case, the width of the packaging sheet may be substantially the same as the width of the absorbent article 1 folded inward or outward along the longitudinal fold lines L0 (that is approximately the same as the width of the body 8).

Also, multiple absorbent articles 1 folded along the longitudinal fold lines L0 may be stacked and packaged together.

This approach makes it possible to package a stack of multiple absorbent articles 1 without much increasing the bulk and carry them in the form of a thin package.

Also, this packaging method makes it possible to reduce the time and effort to take out the absorbent articles 1 from the package and is therefore useful in applications where a large number of absorbent articles 1 are used one after another.

The present application is based on and claims priority to Japanese Patent Application No. 2016-229538 filed on Nov. 25, 2016, the entire contents of which are hereby incorporated herein by reference.

EXPLANATION OF REFERENCE NUMERALS

1 Absorbent article
2 Back-side sheet
3 Upper-side sheet
4 Absorbent
5 Enveloping sheet
7 Side nonwoven fabric
8 Body (absorbent article body)
9 Slip stopper
10 Side areas
11 Rear area
13 Body fluid ejection area
16*a*-16*d* Compressed groove
18 Packaging sheet
19 Releasing sheet
21 First protruding portion
22 Second protruding portion
23 Third protruding portion
31 First recessed portion
32 Second recessed portion
A Intersection between longitudinal fold line and mountain fold line
CL Longitudinal centerline
H Hip-hold portion
L0 Longitudinal hold line
L1 First hold line
L2 Second hold line
L3 Third hold line
M Middle portion
S Underwear
W Wing portion
WG Wing
Y Mountain fold line

The invention claimed is:

1. An individually-packaged absorbent article, comprising:
an absorbent article including a body that includes a permeable upper-side sheet, an impermeable back-side sheet, and an absorbent disposed between the upper-side sheet and the back-side sheet; and
a packaging sheet that individually packages the absorbent article, wherein the body has a shape having a predetermined length in a longitudinal direction and a predetermined width in a direction orthogonal to the longitudinal direction;
the absorbent article includes a hip-hold portion that includes a side area protruding from a rear side-edge of the body, the side area including a first protruding portion that includes a portion having a largest width from a longitudinal centerline of the body, a first recessed portion adjacent to a rear end of the first protruding portion, and a second recessed portion adjacent to a front end of the first protruding portion;
the absorbent article is folded such that a mountain fold line is formed in the side area of the hip-hold portion; and
the mountain fold line intersects with an edge of the side area of the hip-hold portion at a position between a first inflection point between the first recessed portion and the first protruding portion and a second inflection point between the first protruding portion and the second recessed portion, and is substantially orthogonal to the longitudinal centerline.

2. The individually-packaged absorbent article as claimed in claim 1, wherein
the side area of the hip-hold portion is folded along a longitudinal fold line extending in the longitudinal direction; and
each of
an angle formed between the mountain fold line and a straight line that passes through an intersection point of an extension of the mountain fold line with the longitudinal fold line and a bottom point of the first recessed portion, and
an angle formed between the mountain fold line and a straight line that passes through the intersection point and a bottom point of the second recessed portion
is between 30 degrees and 60 degrees.

3. The individually-packaged absorbent article as claimed in claim 2, wherein
a slip stopper for fixing the absorbent article is provided on the back-side sheet in the side area; and
the slip stopper is disposed to cross the straight line passing through the intersection point and the bottom point of the second recessed portion.

4. An absorbent article, comprising:
a body that includes a permeable upper-side sheet, an impermeable back-side sheet, and an absorbent disposed between the upper-side sheet and the back-side sheet, wherein
the body has a shape having a predetermined length in a longitudinal direction and a predetermined width in a direction orthogonal to the longitudinal direction;
the absorbent article further comprises a hip-hold portion that includes a side area protruding from a rear side-edge of the body, the side area including a first protruding portion that includes a portion having a largest width from a longitudinal centerline of the body, a first recessed portion adjacent to a rear end of the first protruding portion, and a second recessed portion adjacent to a front end of the first protruding portion;
a mountain fold line is formed in the side area of the hip-hold portion; and
the mountain fold line intersects with an edge of the side area of the hip-hold portion at a position between a first inflection point between the first recessed portion and the first protruding portion and a second inflection point between the first protruding portion and the second recessed portion, and is substantially orthogonal to the longitudinal centerline.

5. A method of folding an absorbent article that includes a body including a permeable upper-side sheet, an impermeable back-side sheet, and an absorbent disposed between the upper-side sheet and the back-side sheet, the body having a shape that has a predetermined length in a longitudinal direction and a predetermined width in a direction orthogonal to the longitudinal direction, the absorbent article including a hip-hold portion that includes a side area protruding from a rear side-edge of the body, and the side area including a first protruding portion that includes a portion having a largest width from a longitudinal centerline of the body, a first recessed portion adjacent to a rear end of the first protruding portion, and a second recessed portion adjacent to a front end of the first protruding portion, the method comprising:

folding the absorbent article such that a mountain fold line is formed in the side area of the hip-hold portion, wherein the mountain fold line intersects with an edge of the side area of the hip-hold portion at a position between a first inflection point between the first recessed portion and the first protruding portion and a second inflection point between the first protruding portion and the second recessed portion, and is substantially orthogonal to the longitudinal centerline.

* * * * *